United States Patent [19]

McCabe et al.

[11] Patent Number: 4,828,600
[45] Date of Patent: May 9, 1989

[54] BIOLOGICAL INOCULANT FOR CORN

[75] Inventors: Dennis E. McCabe, Middleton; Steven G. Platt, Madison; Alan S. Paau, Middleton, all of Wis.

[73] Assignee: Cetus Corporation, Emeryville, Calif.

[21] Appl. No.: 79,090

[22] Filed: Jul. 29, 1987

[51] Int. Cl.$^4$ .......................... A01N 63/04; C05G 3/00
[52] U.S. Cl. ............................................. 71/76; 71/79; 71/6; 71/903; 71/904; 47/57.6; 435/254
[58] Field of Search ....................... 71/1, 11, 6, 76, 79; 435/254; 47/57.6

[56] References Cited

U.S. PATENT DOCUMENTS 4,061,488  12/1977  Mann ..................................... 424/93
4,438,593  3/1984  McNew ................................. 424/80
4,489,161  12/1984  Papauizas .............................. 424/93
4,668,512  5/1987  Lewis et al. .......................... 424/93

OTHER PUBLICATIONS

Kommehl, Thor et al., "Variability In Performance of Biological and Fungicial Seed Treatments in Corn, Peas, and Soybeans", *Protection Ecology*, 3 (1981), 55-61.

Primary Examiner—Ferris H. Lander
Attorney, Agent, or Firm—Nicholas J. Seay; Philip L. McGarrigle; Albert P. Halluin

[57] ABSTRACT

A biological inoculant is disclosed for facilitating and fostering the growth of edible corn plants. The inoculant includes spores of strains of *Trichoderma hamatum* and *Trichoderma harzianum*, with or without a carrier.

7 Claims, No Drawings

BIOLOGICAL INOCULANT FOR CORN

FIELD OF THE INVENTION

The present invention relates to inoculants for improved cultivation and yield of field crops in general, and relates, in particular, to a biological inoculant to facilitate the germination and growth of edible corn plants.

BACKGROUND OF THE INVENTION

It has long been known in the agricultural arts that certain biological, i.e. microbial, inoculants can be used with certain specific crop species to facilitate the growth of crop plants of that species or to assist the crops of that species in resistance to particular pathogenic organisms. For example, it has long been a common practice to inoculate soybeans and other legumes at plantings with bacterial cultures of the genus Rhizobium, so that the resulting Rhizobium cultures will nodulate within the roots of the soybean or other legumes to form colonies which will fix nitrogen symbiotically for the plant as well as the bacteria.

It has also been known in the prior art that many fungi are often found in association with the roots of many plants. The type of association is poorly understood and there is no clear understanding or agreement among mycologists as to which of such associations are symbiotic and which may be more properly termed pathogenic. The association produced by a fungal on the roots of a plant is referred to as a mycorrhizal association. In a mycorrhizal association, the hyphae of the fungal colony become interwoven with the plant root and root hairs in a poorly understood interaction. Such interactions have generally not been used for any specific benefit except that, in some circumstances, mycorrhizal cultivation of a fungus with a plant can be used to produce the fungus for food purposes. For example, a method is described in U.S. Pat. No. 4,345,403 to generate plants which are mycorrhizated with symbiotic fungi for the purposes of generating fungi for consumption.

It has also been reported specifically that some specific fungi have some capability to be antagonists for plant pathogens. For example, it has been reported that the fungus *Talaromyces flavus* has a capacity to be an antagonist for the fungal pathogen *Verticillium dahliae* in the cultivation of egg plant. Marois, et al., "Biological Control of Verticillium Wilt of Egg Plant Solanum-Melonjena in the Field", *Plant Diseases*, 66:12, pages 1166–1168 (1982). The use of the *T. flavus* inoculation was also reported, in that article, to result in an increased yield of fruits from the plant. The yield increase is described in the antagonistic effect of *T. flavus* on the verticillium species, although even the mechanism by which this effect is accomplished is not at all characterized or understood. In U.S. Pat. No. 4,259,317 a preparation for the protection of emerging sugar beets against damping-off, which is caused by a parasitic fungus, is disclosed which includes the use of the fungus *Pythium oligandrum* which is used as an inoculant on the sugar beet seed to prevent damage to the plant by other fungal species.

It has also been recognized that the Trichoderma fungus may be beneficial to certain edible crops. In one report, Papavizas, "Survival of Trichoderma-Harzianum in Soil and in Pea Pisum-Sativum Cultivar Perfectid-Freezer and Bean Phaseolus-Vulgaris Cultivar Blue-Lake". *Phytopathology*, 72:1, pp. 121–125 (1982), it was reported that the fungus *Trichoderma harzianum* could be isolated from soil and cultivated with pea and bean seedlings in soil. No teaching is presently known for the use of any species of Trichoderma fungi as an inoculant for corn.

SUMMARY OF THE INVENTION

The present invention is directed to improving the growth of plants of edible corn, which includes the step of incorporating into the planting soil, into which the corn seeds are sown, a biologically effective culture of propagules of select species of the Trichoderma fungi. The Trichoderma fungi are selected from one or more biologically pure fungal inoculants from the group of *Trichoderma hamatum* (Bonord.) Bain and *Trichoderma harzianum* Rifai and mutations thereof.

The present invention is also directed to corn seeds which can be coated with a coating including viable propagules of select species of the Trichoderma fungus to aid in the stand and yield from corn plants cultivated from those seeds.

It is an object of the present invention to provide an inoculant effective for the facilitation of germination and growth of edible corn plants.

It is another object of the present invention to provide a completely biological agent that will result in improved grain yield from corn cultivation without additional chemical agents.

Other objects, advantages and features of the present invention will become apparent from the following specification when taken in conjunction with the accompanying claims.

DETAILED DESCRIPTION OF THE INVENTION

The present invention is directed to increasing the corn grain yield by use of a fungal inoculant selected from biologically pure propagules of selected strains *T. hamatum*, *T. harzianum*, and mixtures of these two Trichoderma strains.

Both of these strains were isolated natively from the field and were found existing in close association with the roots of successful corn plants. Their beneficial effect on the growth and yield of corn plants was tested and verified by both greenhouse and field tests.

The *T. hamatum* strain is characterized by the following morphological description:

Hyphae form intercolony chlamydospores
Conidiophores with sterile hyphal elongations
Phialides arise in clusters or sometimes singly, short, plump to pear shaped
Phialospospores green, variable in size: 4–6×2 microns The *T. harzianum* strain is characterized by the following morphological description:

Hyphae form chlamydospores
Conidiophores without sterile hyphal elongation
Phialides regularly formed on dendroid branches of conidiophore
Phialospores globose, subglobose or short obovoid, 3×2.5 microns average To enable others to obtain a culture of this strain of *T. hamatum* (Bonord.) Bain, a sample of this *T. hamatum* has been deposited with the American Type Culture Collection (ATCC), accession number 20,829 on Jan. 22, 1987, and with the Cetus Master Culture Collection (CMCC), accession number 2389. A sample of this strain of *T.harzianum* Rifai spores has likewise been deposited with the ATCC, accession number 20,830, on Jan. 22, 1987, and with the CMCC, accession number 2390.

The fungal inoculants of the present invention act, through an unknown mechanism, to facilitate the germination and growth of plants of edible corn. While the mechanism by which these fungal inoculants facilitate the germination and growth of corn plants is not very well understood, it is possible, that the action involves an antagonistic action of the Trichoderma fungi for other fungal pathogens which may inhibit and/or retard the germination and growth of corn seedlings. The method of action may alternatively involve a symbiotic relationship of some unknown type.

It is broadly intended within the scope of the present invention that the fungal inoculant of the present invention be inoculated into the soil with corn seeds so that a mycorrhyzated culture of the fungi will develop in the root system of the corn plant as it grows. To facilitate this co-culturing, it is preferred that viable propagules of the inoculant, preferably diluted with a suitable extender or carrier, either be applied to the seeds prior to planting or be introduced into the seed furrows at the time of planting the corn seeds. The propagules so delivered may be solely spores or may be any other viable fungal culture capable of successful propagation in the soil. One advantageous technique is that the propagules be applied to the seeds, through the use of a suitable coating mechanism or binder or which there are several known to the art, prior to the seeds being sold into commerce for planting.

Alternatively, the fungal propagules with or without a carrier can be sold as a separate inoculant to be inserted directly into the furrows into which the corn is planted as the corn is planted. Whether the propagules are coated actually on the corn seeds or are inserted into the furrows, the propagules are preferably diluted with a suitable carrier or extender so as to make the cultures easier to handle and to provide a sufficient quantity of material so as to be capable of easy human handling. It has been discovered that clay materials provide an advantageous class of suitable carrier substances for propagules of the Trichoderma fungi, although other suitable carriers are available. It is believed that many non-toxic and biologically inert substances of dried or granular nature are capable of serving as a carrier for the propagules of the fungal inoculant.

The density of inoculation of these fungal cultures onto the seed or into the furrow should be sufficient to populate the sub-soil region adjacent to the roots of the corn plants with viable fungal growth. An effective amount of fungal propagules should be used, such as suggested in the examples below. An effective amount is that amount sufficient to establish sufficient fungal growth so that corn grain yield is increased.

As stated above, these fungal strains were isolated from the roots of exceptionally vigorous corn plants grown under conventional corn cultivations practice. Once the isolation of the strains was made, the fungal culture had to be cultivated to generate sufficient quantities of propagatable fungal material, referred to as propagules, for crop or seed treatment. A typical culture was based on a dextrose-yeast extract.

Once a sufficient quantity of culture of the Trichoderma strains was made, the cultures were recovered by methods known to the art and incubated at room temperature for four to five hours followed by incubation at a relatively low temperature, approximately 4° C. at a high humidity for 18 hours. The cultures were then air-dried at ambient room temperature. The dried cultures may be ground and stored in a dried form suitable for use as a crop inoculant.

It is broadly intended within the scope of the present invention that either of these strains of *T.hamatum*, *T.harzianum*, respectively or mixtures of these Trichoderma strains be used as a fungal inoculant for corn plants in the present invention. The fungal inoculant may be inoculated into the soil with corn seeds so that a mycorrhyzated culture of the fungal inoculant will develop in the root system of the corn crop as it grows. To facilitate this co-culturing, the viable propagules of the fungal inoculant, preferably diluted with a suitable extender or carrier, can either be applied to the seeds prior to planting or be introduced into the seed furrows at the time of planting the corn crop. It is preferred that the propagules be applied to the seeds through the use of a suitable coating mechanism or binder, of which there are several known to the art, prior to the seeds being sold into commerce for planting. Alternatively, the propagules with or without a carrier can be sold as a separate inoculant to be inserted directly into the furrows into which the corn is planted.

It has been discovered here that the inoculation of the two *T.hamatum* and *T.harzianum* strains with corn plants results in significantly improved growth of corn plants. As will be appreciated by any person skilled in plant husbandry, the rate of growth or improvement in growth of any given crop is subject to many variables. It has been found here, however, that the co-cultivation of the fungal inoculants of the present invention with edible corn plants is of significant advantage in at least some typical field conditions. It is believed that this co-cultivation technique will result generally in improved yield and improved growth of corn plants in field applications.

It will be appreciated by one skilled in the art that a biological inoculant of the type described herein offers several significant potential advantages over the chemical inoculants or growth hormones or similar agents commonly used in agriculture today. By the very nature of the fungal inoculant, it is capable of sustaining itself in a continuous fashion once initial spores are introduced into the furrows with the corn seeds; thus, there is no need for retreatment of the plants during the crop season. The fungus grows in cultivation along with the plants and should continue to exhibit its beneficial effect on the plant throughout the agricultural season. This is in strong contrast to chemical growth agents or fungicides which must be retreated periodically to have a continuing effect on inhibition on the fungus in question or to help improve the plant growth throughout its life cycle. Because the fungal inoculant of the present invention can be inoculated onto the seeds through spores in a dry formulation, the application of this technique is relatively simple to the farmer since the seeds can be inoculated prior to distribution. In this way, a significant economic advantage over the field treatments of cultivated corn crops with agricultrual chemicals is achievable.

The following non-limitative examples are intended to illustrate the present invention.

Example 1

The Trichoderma species which make up the fungal inoculant of the present invention were isolated as intimate root-associates from corn plant roots in a field in Iowa. The culture was grown in a liquid medium containing dextrose-yeast extract to create crop inoculating propagules in accordance with the methods described above. The propagules were then formulated into a dry inoculant containing Pyrax ® as a carrier.

The dry fungal propagules were then either applied in seed furrow or coated onto the seeds with polyvinylpyrrolidone 40,000. The seeds were planted in a soil mix, either of the Batavia soil type, or Kegonsa soil type, and grown in a greenhouse for approximately four to six weeks. The values shown in the table below were obtained by comparing the average dry weight of 8 treated plants to the average dry weight of 16 untreated plants.

TABLE 1

Changes in Dry-Shoot Weight of Corn by Inoculations of T. hamatum and T. harzianum in Combination

| Test | Conditions | Percent Change |
|---|---|---|
| 1 | $N^1, B^2, F^3$ | 29 |
| 2 | N,B,F | 12 |
| 3 | N,B,F | 8 |
| 4 | $N, K^4, F$ | −4 |
| 5 | $N, B, C^5$ | 17 |
| 6 | N,B & K,F | −7 |
| 7 | $D^6, B, F$ | 5 |
| 8 | D,B,F | −1 |
| 9 | D,K,F | 2 |
| 10 | D,B,C | 18 |
| 11 | D,B & K,F | −5 |
| Average % Change | All tests | $6.730^7$ |
| Average % Change | N only | $9.170^8$ |
| Average % Change | D only | $3.300^9$ |

[1] N—Normal greenhouse conditions
[2] B—Batavia soil type
[3] F—Inoculant applied in seed furrow
[4] K—Kegonsa soil type
[5] C—Inoculant applied by precoating seed with dried microbes
[6] D—Simulated drought conditions
[7] P = 0.039
[8] P = 0.077
[9] P = 0.193

Example 2

Seven field tests of corn were planted in which half of the plants were inoculated with microbes from T.hamatum and T.harzianum dried in Pyrax and coated onto the seeds with polyvinylpyrrolidone 40,000. The other half, i.e. the control seeds, were only coated with polyvinylpyrrolidone 40,000. After the growing season, the treated corn showed an average increase of 6.6 bushels per acre (B/A), amounting to a 4.4% average increase in yield. The results of the seven tests are listed in Table 2 below.

TABLE 2

Yield Improvement of Corn by Inoculations of T. hamatum and T. harzianum

| Test | Control Yield (B/A) | Treated Yield (B/A) | B/A Yield Difference | % Yield Change |
|---|---|---|---|---|
| 1 | 154.9 | 179.5 | 24.6 | 15.9 |
| 2 | 157.9 | 164.1 | 6.2 | 3.9 |
| 3 | 82.5 | 85.1 | 2.6 | 3.2 |
| 4 | 159.5 | 162.7 | 3.2 | 2.0 |
| 5 | 98.5 | 100.8 | 2.3 | 2.3 |
| 6 | 106.7 | 102.9 | −3.8 | −3.6 |
| 7 | 160.0 | 170.9 | 10.9 | 6.8 |
| Average | 131.4 | 138.0 | 6.6 | 4.4 |

Example 3

Fifteen additional field tests were conducted in a manner similar to Example 2, with the exception that the microbes dried in Pyrax were coated onto the seeds with natural rubber cement (resin in hexane). The average increase of the treated fields as opposed to the control fields was 6.5 bushels per acre, which is a 4.2 percent average yield increase. The individual field tests and their results are listed below in Table 3.

TABLE 3

Yield Improvement of Corn by Inoculations of T. hamatum and T. harzianum

| Test | Control Yield (B/A) | Treated Yield (B/A) | B/A Yield Difference | % Yield Change |
|---|---|---|---|---|
| 1 | 116.6 | 121.1 | 4.5 | 3.9 |
| 2 | 132.5 | 134.9 | 2.4 | 1.8 |
| 3 | 152.3 | 158.5 | 6.2 | 4.1 |
| 4 | 168.8 | 176.0 | 7.3 | 4.3 |
| 5 | 185.3 | 186.9 | 1.6 | 0.9 |
| 6 | 162.0 | 171.8 | 9.8 | 6.1 |
| 7 | 108.3 | 122.2 | 14.0 | 12.9 |
| 8 | 206.8 | 203.7 | −3.1 | −1.5 |
| 9 | 137.7 | 156.0 | 18.2 | 13.2 |
| 10 | 108.5 | 110.6 | 2.1 | 2.0 |
| 11 | 159.3 | 153.9 | −5.5 | −3.4 |
| 12 | 187.4 | 218.3 | 30.9 | 16.5 |
| 13 | 174.9 | 174.1 | −0.8 | −0.5 |
| 14 | 163.5 | 166.7 | 3.3 | 2.0 |
| Average | 154.5 | 161.0 | 6.5 | 4.4 |

The above cultures of T. hamatum and T. harzianum were deposited with the American Type Culture Collection, 12301 Parklawn Drive, Rockville, MD, USA, on Jan. 22, 1987. The accession numbers are as follows.

| Culture | CMCC | ATCC |
|---|---|---|
| T. hamatum | 2389 | 20829 |
| T. harzianum | 2390 | 20830 |

The above deposits were made pursuant to a contract between the ATCC and Cetus Corporation, a partner in the assignee of the present invention. The contract with the ATCC provides for permanent availability of the cultures of these fungi to the public on the issuance of the U.S. patent describing and identifying the deposit or publication on laying open to the public of any U.S. or foreign patent application, whichever comes first, and for the availability of these cultures to one determined by the U.S. Commissioner of Patents and Trademarks to be entitled thereto according to 35 USC Section 122 and the Commissioner's rules pursuant thereto (including 37 CFR Section 1.14 and 886 O.G. 638). The assignee of the present invention has agreed that if the cultures on deposit should die or be lost or destroyed when cultivated under suitable conditions, they will promptly be replaced on notification with viable cultures of the same fungi.

It is to be understood that modifications and variations may be resorted to with respect to the present invention without departing from the spirit and scope of this invention as those skilled in the art will readily understand. Thus, the present invention should not be limited to the above-described specification, but should be interpreted in accordance with the following claims:

What is claimed is:

1. A biological inoculant for fostering the growth of corn comprising spores of at least one biologically pure fungal culture selected from the group consisting of *Trichoderma hamatum* (Bonord) Bain (ATCC accession No. 20,829), *Trichoderma harzianum* Rafia (ATCC accession No. 20,830) and corn yield enhancing mutations thereof, and a carrier.

2. The biological inoculant according to claim 1 wherein the carrier is a clay material.

3. Edible corn seed coated with a coating comprising spores of at least one biologically pure fungal culture selected from the group consisting of *Trichoderma hamatum* (Bonord) Bain (ATCC accession No. 20,829), *Trichoderma harzianum* Rafia (ATCC accession No. 20,830) and corn yield enhancing mutations thereof, and a carrier.

4. Edible corn seeds according to claim 3 wherein the coating also includes a carrier for the spores.

5. An agriculturally useful composition comprising a corn seed and a coating on the seed including at least one biologically pure fungal culture selected from the group consisting of *Trichoderma hamatum* (Bonord) Bain (ATCC accession No. 20,829), *Trichoderma harzianum* Rafia (ATCC accession No. 20,830) and corn yield enhancing mutations thereof.

6. The agriculturally useful composition according to claim 5 further including in the coating a carrier.

7. A method of improving the growth of plants of edible corn seeds comprising the step of introducing into the furrow into which the corn seeds are sown an effective amount of spores of a biologically pure fungal inoculant selected from at least one of the group consisting of *Trichoderma hamatum* (Bonord) Bain (ATCC accession No. 20,829), *Trichoderma harzianum* Rafia (ATCC accession No. 20,830), and corn yield enhancing mutations thereof, and a carrier.

* * * * *